(12) United States Patent
Jeong et al.

(10) Patent No.: US 6,944,496 B2
(45) Date of Patent: Sep. 13, 2005

(54) APPARATUS FOR POSITIONING AND MARKING A LOCATION OF AN EMG ELECTRODE

(75) Inventors: Hyuk Jeong, Daejeon (KR); Hyun Bin Kim, Daejeon (KR); Ki Ho Kim, Daejeon (KR); Ki Hong Kim, Daejeon (KR); Hong Kee Kim, Daejeon (KR); Hyun Myung, Daejeon (KR); Sang Won Ghyme, Jeju-do (KR); Ki Suk Lee, Seoul (KR); Yong Wan Kim, Daejeon (KR); Jin Sung Choi, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 569 days.

(21) Appl. No.: 10/095,723

(22) Filed: Mar. 13, 2002

(65) Prior Publication Data

US 2003/0125636 A1 Jul. 3, 2003

(30) Foreign Application Priority Data

Dec. 27, 2001 (KR) ........................................ 2001-85802

(51) Int. Cl.⁷ .......................................... A61B 5/0488
(52) U.S. Cl. ..................................................... 600/546
(58) Field of Search .......................................... 600/546

(56) References Cited

U.S. PATENT DOCUMENTS

| | | | | | |
|---|---|---|---|---|---|
| 4,170,225 | A | * | 10/1979 | Criglar et al. | ............... 600/546 |
| 6,076,011 | A | * | 6/2000 | Hoover | ........................ 600/546 |
| 6,289,245 | B1 | | 9/2001 | Mo et al. | |

FOREIGN PATENT DOCUMENTS

| | | | | |
|---|---|---|---|---|
| EP | 0938911 | 12/2000 | ............ | A61N/1/36 |
| KR | 99-66565 | 8/1999 | ............ | G08B/3/00 |
| KR | 00-72178 | 12/2000 | ............ | A61B/5/04 |

* cited by examiner

Primary Examiner—Kennedy Schaetzle
Assistant Examiner—Kristen Mullen
(74) Attorney, Agent, or Firm—Mayer, Brown, Rowe & Maw LLP

(57) ABSTRACT

An apparatus for positioning and marking a location of an electromyography (EMG) electrode includes a housing having a back surface, an EMG sensor for receiving the EMG signal, an amplifying circuit for amplifying the EMG signal to generate an amplified EMG signal and an audio output terminal for outputting the amplified EMG signal as the audio EMG signal. The examinee may directly position and mark the location of the EMG electrode and may easily detect the fatigue rate of the muscle or the abnormal condition of the muscle by using the sound of the audio equipment.

4 Claims, 5 Drawing Sheets

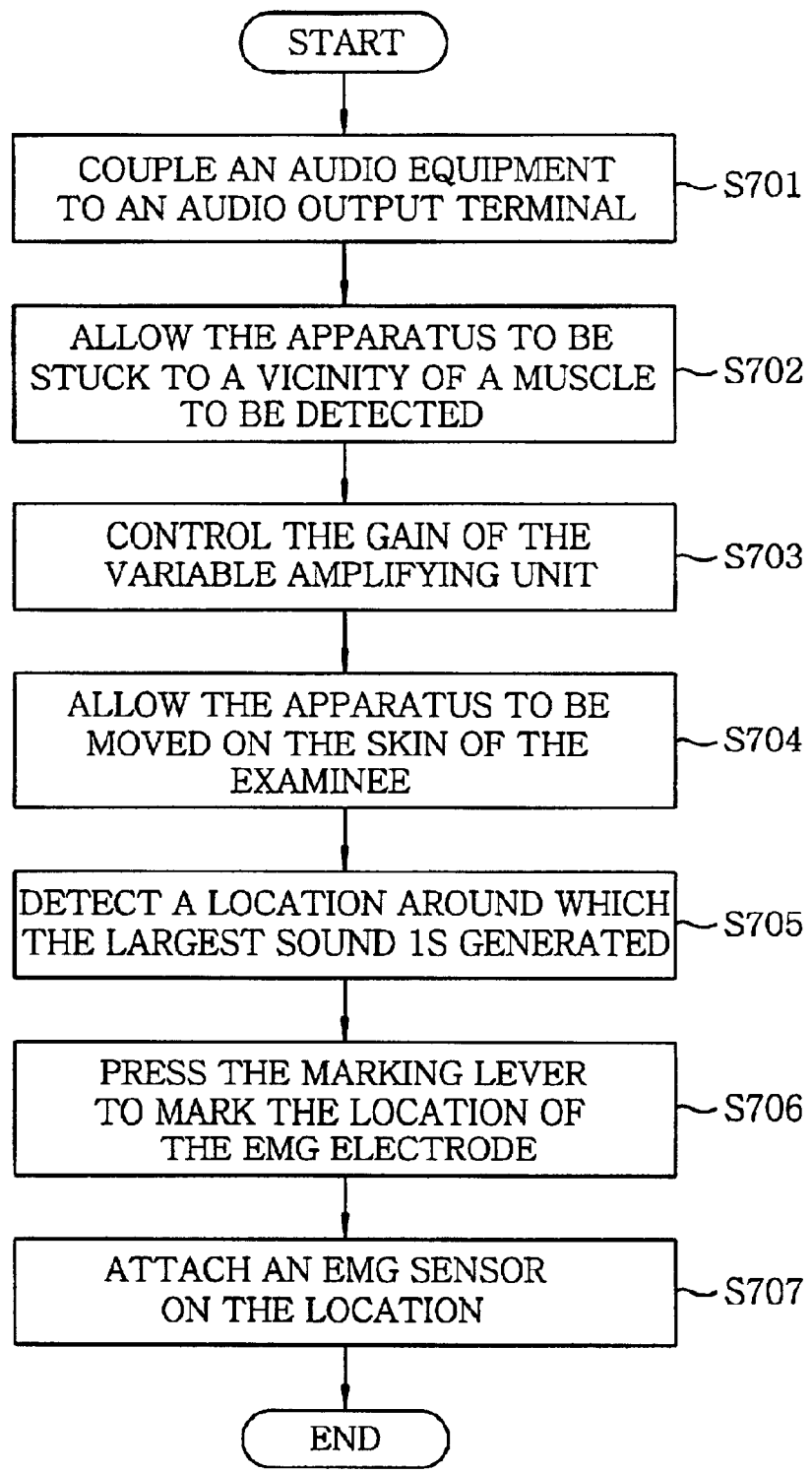

APPARATUS FOR POSITIONING AND MARKING A LOCATION OF AN EMG ELECTRODE

FIELD OF THE INVENTION

The present invention relates to an apparatus for positioning and marking a location of an electromyography (EMG) electrode, and, more particularly, to an apparatus for converting an EMG signal to an audio EMG signal to easily position a location of an EMG electrode and to easily mark the location thereof on a skin of a human body.

BACKGROUND OF THE INVENTION

The EMG signal represents an electrical signal associated with an activity of a skeletal muscular fiber and has been used to control a prosthesis or to develop a human computer interface (HCI) technology.

In order to control the prosthesis to develop an EMG based HCI technology, a sensor to detect the EMG signal must be attached around a portion, e.g., an arm, of a body. Since the inaccurate location of the EMG electrode results in a malfunction of the prosthesis or the HCI due to a noise of the body itself, the location of the EMG electrode must be precisely detected depending on the motion of the body, e.g., a bending of an arm.

Accordingly, an examiner, e.g., an anatomist is required to detect the location of the EMG electrode depending on the motion of the body. Since the prosthesis or the HCI apparatus must be occasionally attached or detached as necessity requires, it is difficult for the examinee himself/herself to detect the location of the EMG electrode.

In order to overcome such difficulty, an instant power of the EMG electrode to be detected is displayed on an light emitting diode (LED) so that the level of the LED may be used to determine the location of the EMG electrode. Accordingly, the location of the EMG electrode was directly measured by the eyes or directly marked with a pen on the skin of the examinee.

Since, however, an EMG sensor is usually attached around one arm of the examinee, it is more difficult for the examinee to determine the location of the EMG electrode and to mark same with a pen taken in the hand of the other arm of the examinee on which no EMG sensor is attached. Further, if a frequency modulation procedure is used to determine the fatigue rate of the muscle or the abnormal condition of the muscle, an additional apparatus such as a frequency analyzer must be required.

SUMMARY OF THE INVENTION

It is, therefore, an object of the present invention to provide an apparatus for positioning and marking a location of an EMG electrode to easily position a location of an EMG electrode depending on a motion of the body of an examinee and to easily mark the location of the EMG electrode on the skin of an examinee by using the fact an auditory organ, i.e., an ear, has a frequency analyzing function as well as a level analyzing function.

In accordance with a preferred embodiment of the present invention, there is provided an apparatus for positioning and marking a location of an electromyography (EMG) electrode to convert an EMG signal to an audio EMG signal, comprising:

a housing having a back surface;

an EMG sensor, installed on the back surface of the housing, for receiving the EMG signal, wherein the EMG sensor has a sensing surface capable of being contacted with a human body;

an amplifying circuit for amplifying the EMG signal to generate an amplified EMG signal; and an audio output terminal, installed on a side of the housing, for outputting the amplified EMG signal as the audio EMG signal, wherein the audio output terminal has a structure capable of being connected with an audio input terminal of a audio device.

BRIEF DESCRIPTION OF THE DRAWINGS

The above and other objects and features of the present invention will become apparent from the following description of preferred embodiments given in conjunction with the accompanying drawings, in which:

FIG. 4 describes a flow chart for illustrating a using procedure of the apparatus for positioning and marking the location of the EMG electrode in accordance with the present invention.

DETAILED DESCRIPTION OF THE PREFERRED EMBODIMENTS

Figure 1A:
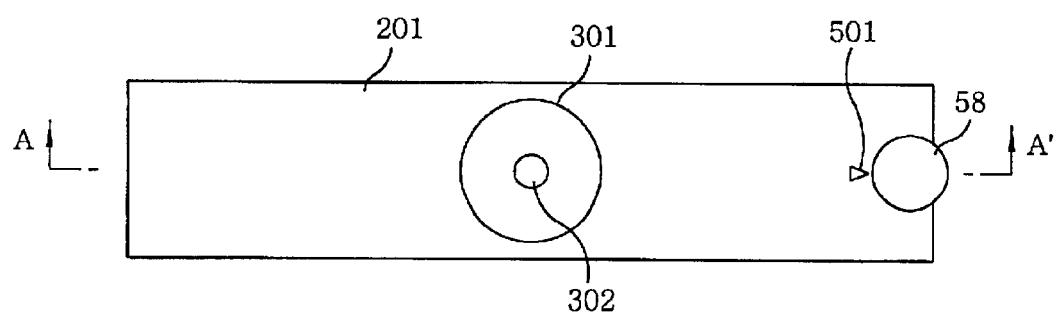
FIGS. 1A to 1D represent a plan view, a cross-sectional view taken along a line A–A', a back view and a right side view of an apparatus for positioning and marking a location of an electromyography (EMG) electrode in accordance with the present invention, respectively.
Figure 1B:
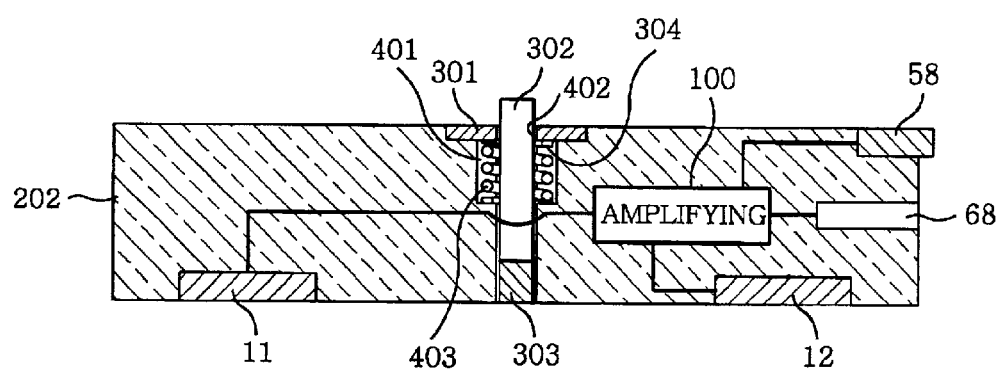
Figure 1C:
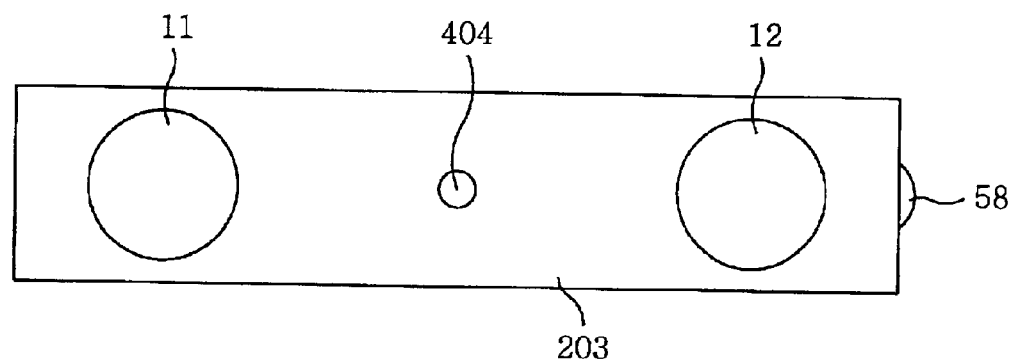
Figure 1D:
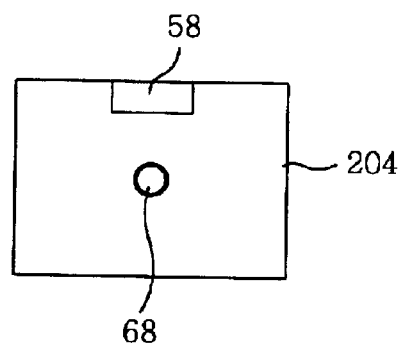

Referring to FIGS. 1A to 1D, there is shown a schematic view for an apparatus for positioning and marking a location of an electromyography (EMG) electrode in accordance with the present invention. FIGS. 1A to 1D represent a plan view, a cross-sectional view taken along a line A–A', a back view and a right side view of the apparatus in accordance with the present invention, respectively.

The apparatus includes a rectangular parallelepiped housing 201, 202, 203 and 204, a first and a second EMG sensors 11 and 12, an amplifying circuit 100, a gain control lever 58, an audio output terminal 68, a marking lever 302, a marking tap 303, an elastic material housing space 401, an elastic material 403 and a marking lever cap 301.

The first and the second EMG sensors 11 and 12 for receiving a first and a second EMG signals are installed on a back surface of the housing 201, 202, 203 and 204 and each of the first and the second EMG sensors 11 and 12 has a sensing surface which may be contacted with a human body. It is preferable that at least two EMG sensors receive at least two EMG signals around at least two different points, respectively.

The amplifying circuit 100 is installed in the housing 201, 202, 203 and 204 and amplifies the first and the second EMG signals to a predetermined level to generate an amplified EMG signal. The gain control lever 58 is installed on a side of the housing 201, 202, 203 and 204 and may be rotated to control a gain of the amplifying circuit 100. The audio output terminal 68 is installed on a side of the housing 201, 202, 203 and 204 and outputs the amplified EMG signal as an audio EMG signal. The audio output terminal 68 has a structure capable of being connected to an audio input terminal of an audio device.

The marking lever 302 is installed within a lever guide conduit 402 formed through a central region of the housing 201, 202, 203 and 204 and may freely move along the lever guide conduit 402. On an end of the marking lever 302, the marking tap 303 is integrated so that it may be projected outside of the lever guide conduit 402 through a tap hole 404 formed on the back surface of the housing 201, 202, 203 and 204 due to the movement of the marking lever 302.

A projection 304 formed on the marking lever 302 is contacted to the elastic material 403 so that the marking lever 302 may elastically move. The elastic material 403 is inserted in an elastic material housing space 401 formed within the housing 201, 202, 203 and 204. It is preferable that the elastic material housing space surrounds the marking lever 302. The elastic material 403 is covered with the marking lever cap 301 so that not only the elastic material 403 but also the marking lever 302 may be constrained in the elastic material housing space 401.

A gain setup reference 501 may be marked to represent a rotational angle of the gain control lever 58.

Figure 2:
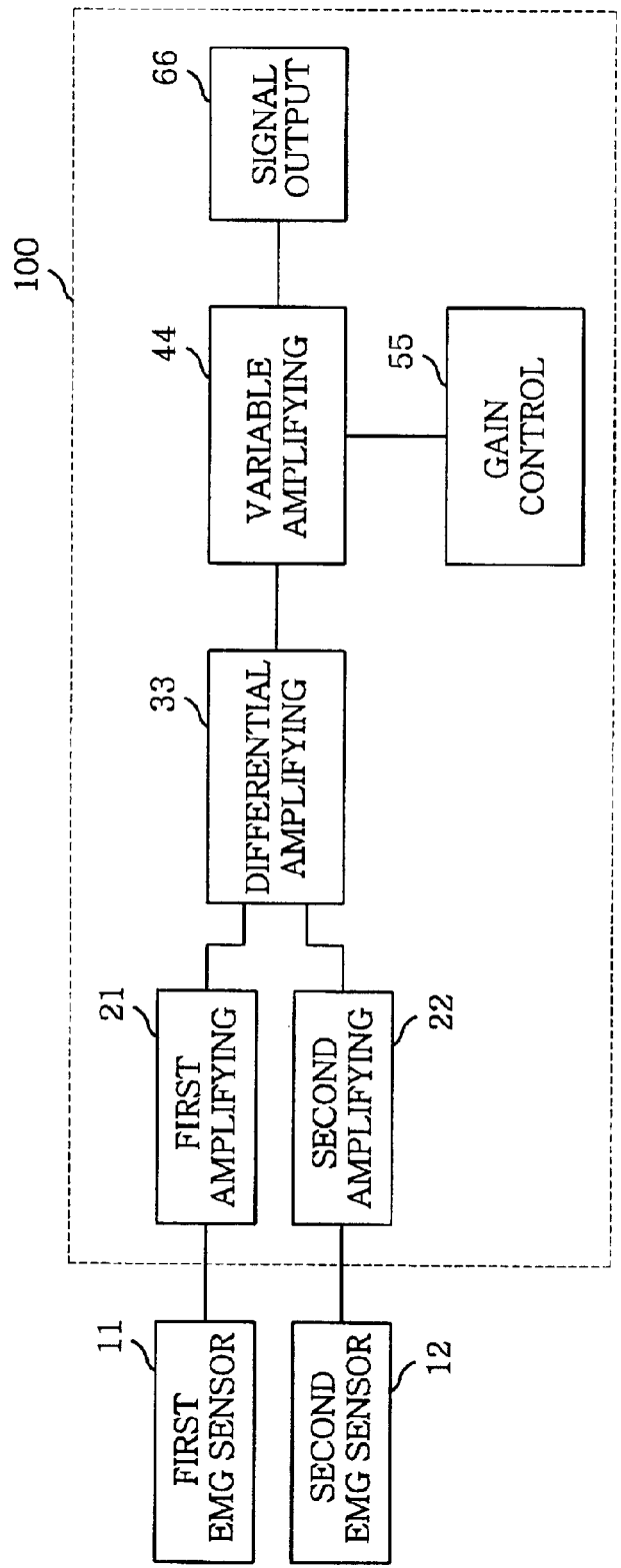
FIG. 2 shows a schematic circuit in the apparatus for positioning and marking the location of the electrode in accordance with the present invention.
Figure 3:
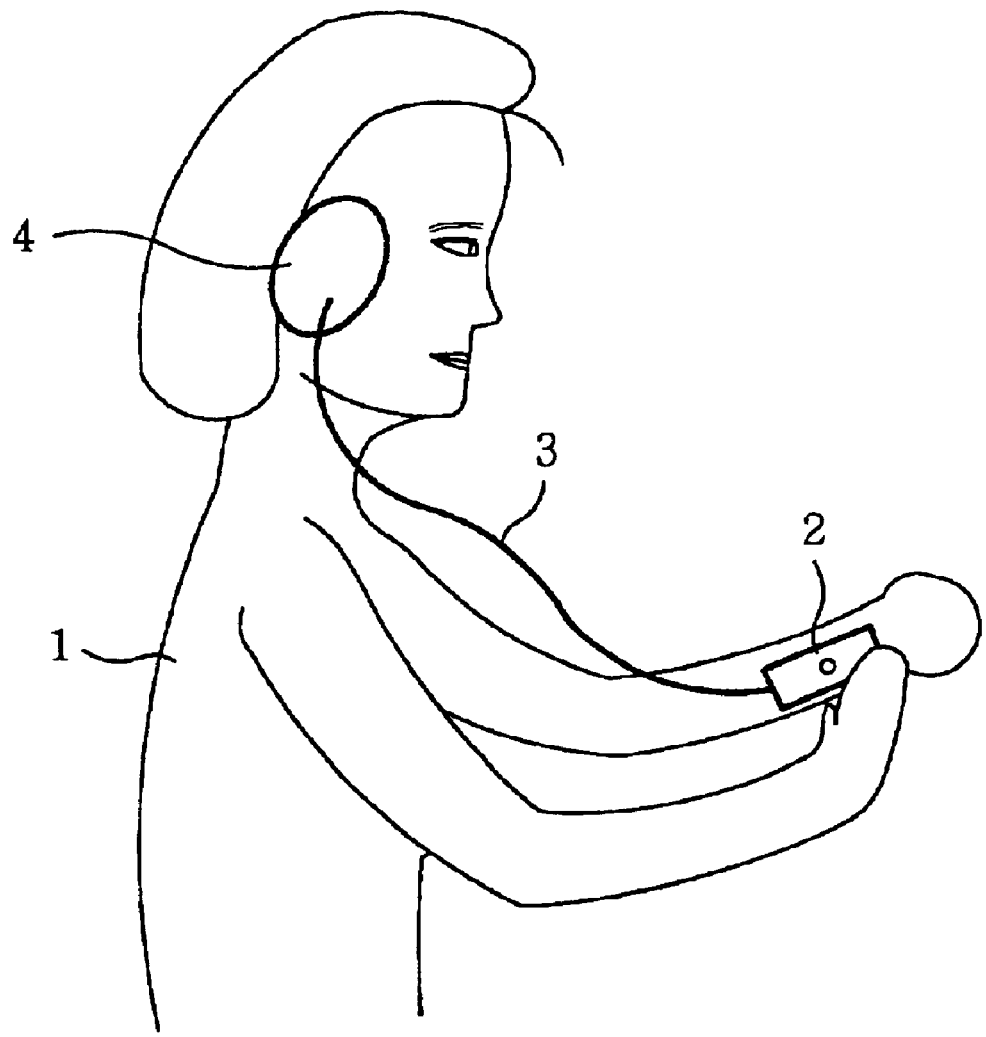
FIG. 3 presents a diagram for illustrating a using practice of the apparatus for positioning and marking the location of the EMG electrode in accordance with the present invention.

Referring to FIG. 2, there is shown a schematic circuit in the apparatus for positioning and marking the location of the EMG electrode in accordance with the present invention. Specifically, the amplifying circuit 100 is illustrated.

A first and a second amplifying units 21 and 22 amplifies the first and the second EMG signals detected by the first and the second EMG sensors 11 and 12 to generate a first and a second amplified EMG signals, respectively.

A differential amplifying unit 33 receives the first and the second amplified EMG signals fed from the first and the second amplifying units 21 and 22 as two inputs and generates a differential amplified EMG signal which corresponds to a difference between the first and the second amplified EMG signals. In other words, the differential amplified EMG signal is in proportion to a variance between the first and the second EMG signals.

A gain control unit 55 generates a variable resistance depending on the rotational angle of the gain control lever 58 shown in FIG. 1 to determine a variable gain of the variable amplifying unit 44. The variable amplifying unit 44 amplifies the differential amplified EMG signal based on the variable gain to generate a variable amplified EMG signal.

A signal output unit 66 transmits the variable amplified EMG signal through the audio output terminal 68 shown in FIG. 1 to an audio equipment such as a headphone.

Referring to FIGS. 1 to 4, there is illustrated a positioning and marking procedure for the location of the EMG electrode by using the apparatus for positioning and marking the location of the EMG electrode.

First, an examinee 1 sets an audio equipment such as a headphone 4 around an audible position, e.g., an ear, and couples a connector attached to an input line 3 of the audio equipment to the audio output terminal 68 of the apparatus 2 in accordance with the present invention (S701).

The examinee allows the apparatus 2 to be closely stuck to a vicinity of a muscle to be detected. The first and the second EMG sensors 11 and 12 may be attached on a skin of the examinee 1 (S702).

The gain control lever 58 is rotated so that the gain of the variable amplifying unit 44 may be controlled. On hearing the sound through the audio equipment, the examinee allows the positioning and marking apparatus 2 to be moved while the apparatus 2 is closely stuck to the skin of the examinee (S703 and S704).

Since the EMG signals detected by the first and the second EMG sensors 11 and 12 are modified as the audio EMG signals to be transmitted to the audio equipment, the examinee may compare the amplitudes of the audio EMG signals to each other to find the location of the EMG electrode.

In order to generate the audio EMG signal from the EMG signals, the first and the second amplifying units 21 and 22 in the amplifying circuit 100 amplifies the first and the second EMG signals detected by the first and the second EMG sensors 11 and 12 to generate the first and the second amplified EMG signals, respectively. The differential amplifying unit 33 generates the differential amplified EMG signal which corresponds to the difference between the first and the second amplified EMG signals. The variable amplifying unit 44 further amplifies the differential amplified EMG signal to generate the variable amplified EMG signal with a predetermined level. The signal output unit 66 transmits the variable amplified EMG signal through the audio output terminal 68 to the audio equipment.

The nearer be the apparatus 2 to the muscle which allows the body to be in motion, the larger be the EMG signal. Since the amplitude of the EMG signal is also in proportion to the intensity of the sound generated through the audio equipment, the location around which the largest sound is generated corresponds to the location of the EMG electrode at which the largest EMG signal to noise is detected (S705).

If the location of the EMG electrode related with the motion of the muscle is determined, the examinee allows the present positioning and marking apparatus to be stuck to the location and presses the marking lever 302. Then the marking lever 302 is caused to move downwards along the lever guide conduit 402 and, therefore, the marking tap 303 is projected out through the tap hole 404. Accordingly, the marking tap 303 is used to put in colors on the skin of the human body to mark the location of the EMG electrode (S706).

If the examinee stops pressing the marking lever 302, the elastic material 403 which was contracted due to the downward motion of the marking lever 302 may be back so as to be restored and the projection 304 imposed on the elastic material 403 may be also moved upwards so that the marking lever 302 may be upwards with the projection 304 attached thereon. The marking lever cap 301 may protect the marking lever 302 from being separated from the housing 201, 202, 203 and 204 by the elastic force of the elastic material 403.

The examinee attaches an EMG sensor to be used in a prosthesis or a HCI apparatus on the location of the EMG electrode marked by the marking tap 303 and allows the prosthesis and the HCI apparatus to be operated (S707).

The examinee is allowed to directly position the location of the EMG electrode by using the apparatus for positioning and marking the location of the EMG electrode in accordance with the present invention. Further, the examinee may easily detect the fatigue rate of the muscle or the abnormal condition of the muscle by using the sound of the audio equipment.

While the invention has been shown and described with respect to the preferred embodiments, it will be understood by those skilled in the art that various changes and modifications may be made without departing from the spirit and scope of the invention as defined in the following claims.

What is claimed is:

1. An apparatus for positioning and marking a location of an electromyography (EMG) electrode to convert an EMG signal to an audio EMG signal, comprising:

a housing having a back surface;

an EMG sensor, installed on the back surface of the housing, for receiving the EMG signal, wherein the EMG sensor has a sensing surface capable of being contacted with a human body;

an amplifying circuit for amplifying the EMG signal to generate an amplified EMG signal;

an audio output terminal, installed on a side of the housing, for outputting the amplified EMG signal as the audio EMG signal, wherein the audio output terminal has a structure capable of being connected with an audio input terminal of a audio device;

a marking lever installed to be capable of moving along a lever guide conduit installed through the housing; and a marking tap, integratedly installed on an end of the marking lever, capable of being projected outside of the housing due to the movement of the marking lever.

2. The apparatus of claim 1, further comprising a gain control unit, installed on a side of the housing, for controlling a gain of the amplifying circuit.

3. The apparatus of claim 2, wherein the EMG sensor has one or more EMG sub-sensors for receiving one or more EMG sub-signals, respectively, and the amplifying circuit includes:

one or more amplifying units for amplifying said one or more EMG sub-signals to generate one or more amplified EMG sub-signals, respectively;

a differential amplifying unit for receiving said one or more amplified EMG sub-signals to output a differential amplified EMG signal which is in proportion to a difference between said one or more amplified EMG sub-signals;

a variable amplifying unit for amplifying the differential amplified EMG signal based on a variable gain which corresponds to a variable resister of the gain control unit to generate a variable amplified EMG signal; and a signal output unit for outputting the variable amplified EMG signal to the audio output terminal.

4. The apparatus of claim 1, further comprising an elastic material for allowing the marking lever to elastically move and wherein the housing has an elastic material housing space for receiving the elastic material.

* * * * *